United States Patent [19]
Magarinos et al.

[11] Patent Number: 5,103,323
[45] Date of Patent: Apr. 7, 1992

[54] MULTI-LAYER HOLOGRAPHIC NOTCH FILTER

[75] Inventors: Jose R. Magarinos, Thornwood, N.Y.; John F. Cueva, Washington, N.J.

[73] Assignee: Holographic Optics, Inc.

[21] Appl. No.: 510,546

[22] Filed: Apr. 18, 1990

[51] Int. Cl.⁵ .............................................. G02B 5/32
[52] U.S. Cl. ........................................ 359/8; 359/19; 359/15; 359/24; 351/44
[58] Field of Search ................. 350/3.6, 3.65, 3.7, 350/3.77, 3.81; 351/44

[56] References Cited

U.S. PATENT DOCUMENTS

| | | | |
|---|---|---|---|
| 4,601,533 | 7/1986 | Moss | 350/3.77 |
| 4,637,678 | 1/1987 | Moss et al. | 350/3.7 |
| 4,786,125 | 11/1988 | Magarinos et al. | 350/3.65 |
| 4,802,719 | 2/1989 | Magarinos et al. | 350/3.65 |
| 4,830,441 | 5/1989 | Chang | 350/3.77 |
| 4,978,182 | 12/1990 | Tedesco | 350/3.7 |

Primary Examiner—Bruce Y. Arnold
Assistant Examiner—J. P. Ryan
Attorney, Agent, or Firm—Handal & Morofsky

[57] ABSTRACT

A holographic member for a helmet visor comprising a first holographic layer having planes of diffraction oriented in a first direction in a given local area is disclosed. A second holographic layer disposed over said first holographic layer has planes of diffraction oriented in said local area in the opposite direction. The first holographic layer is transferred from a slanted planar holographic mirror. The second holographic layer comprises the holographic analog of an oppositely slanted transferred planar mirror. The slant and the opposite slant have substantially the same magnitude of slant but opposite orientation, providing for diffractive ghost compensation. A third holographic layer, unslanted, is transferred from an unslanted planar holographic mirror. The three holographic layers provide practical total eye coverage with minimum diffractive unwanted ghosts.

5 Claims, 5 Drawing Sheets

MULTI-LAYER HOLOGRAPHIC NOTCH FILTER

TECHNICAL FIELD

The invention is concerned with multiple element holographically formed optical notch filters which are of particular value for protecting the eye or other sensitive detectors from high intensity laser radiation when, for example, incorporated in a shield which reflects light within a narrowly defined notch of wavelengths. The inventive method which involves formation of three holographic elements, two of which are locally identical but oppositely oriented, in a flat configuration and transfer to a curved visor is a particularly advantageous construction method and makes possible the high quality objectives of the inventive approach.

BACKGROUND

Holographic mirrors which have the property of reflecting only a band of optical wavelengths have been widely discussed as a means for protection against various laser hazards. Such laser hazards include both those created in the context of military situations on the battlefield or in the air as well as in commercial and industrial facilities. These hazards create a chance of retinal damage as a result of a beam of high intensity laser light reaching the eye of an individual.

In its most general case, a planar mirror formed as a volume phase hologram in an optically sensitive emulsion will, in the simplest case, have the characteristic of reflecting only incident light in a relatively narrow range of wavelengths centered on the wavelength at which the mirror was recorded, provided that light is incident at the same angle at which the mirror was formed. In the simplest case of a planar mirror, this would be light incident at a right angle.

Protective systems of this sort suffer from a number of inadequacies. For example, emulsions presently available are usually sensitive at only one particular laser frequency and other wavelengths at which lasers output light will minimally or substantially not at all expose the photosensitive emulsion. Another problem involves the fact that, in accordance with Bragg's Law, the wavelength range of the notch will vary as a function of the incident angle of incoming radiation. The problem is yet further complicated if the object to be protected moves over a range of particular points, (such as the eye does), and if the shape of the protective member, such as a helmet visor, is curved. In addition, given the fact that such situations define a volume to be protected substantially greater than a point, and the further additional complication of having to provide a reflective notch at a variety of angles for a particular laser wavelength without substantial coloring of the outside world and/or reducing visual transmission to see through the filter, substantial complicating factors exist.

An approach is to widen the bandwidth of the notch filter, thus making it effective over a wide range of angles. This technique has the distinct disadvantage of seriously compromising transmittance of the protective filter at wavelengths other than those at which reflection is desired, thus darkening the view of the outside world and compromising visual acuity in what is often a high criticality situation, as would be the case, for example, in military applications. Widening the notch will also have the undesirable effect of significantly coloring the perception of the outside world.

Still another approach to the problem is the fabrication of the notch filter on a substrate of a given configuration, followed by transfer of the exposed hologram to a substrate of a different configuration (U.S. Pat. No. 4,802,719: Infrared Laser Shield). Also, in my earlier U.S. Pat. No. 4,786,125 entitled Ocular Protection Apparatus, in which this technique is used to minimize the angles of possible laser-light incidence with respect to normals to an optical surface protecting the eye of an individual.

Still yet another approach is the use of a multiple element holographic mirror. Typically, in accordance with this type of solution, the angular characteristics of each of the elements is made different from the other. For example, one of the layers may be designed to protect one of the eyes of an individual while the other layer may be designed to protect the individual's other eye, with both layers disposed over and completely covering a transparent helmet visor.

In particular, one approach that has been proposed is the use of two holograms each of which is designed to protect one of the eyes of an individual who is wearing a visor which incorporates the two holograms. Generally, each of the holographic protective layers will comprise a volume phase hologram in which the planes in the volume of the volume phase hologram form concentric spheres centering on one of the eyes to be protected while the concentric spheres in the other holographic film center on the other eye to be protected. While such an approach would appear to present an ideal solution to the problem, several inadequacies will present themselves.

In particular, as noted above, a visor constructed in accordance with this technique consists of two slanted holograms with a spherical configuration, each having the center of curvature in the safety zone. Moreover, the normals for each hologram are designed to pass through the centers of curvature of the spherical mirrors which form the hologram. However, the slanted configuration of this design creates, by the intersection of planes of diffraction with the surface, an unevenly spaced surface grating. This uneven surface grating produces diffractive ghost images.

In addition to diffracted ghost images produced by the surface grating, both ghosts and flare might be created by secondary holograms recorded in the sensitive holographic emulsion by multiple internal reflections which occur during construction of the interference pattern during exposure of the hologram. This results in multiple recordings and even if anti-reflection coatings are used, such multiple recordings will produce serious ghost images and so-called flare where the tendency is to separate colors of light but not by such a great angular deviation as to generate separate ghost images. Generally, multiple recordings produce ghosts, not by surface diffraction, but by the super imposition of planes of diffraction which are closely recorded in space.

If we consider these problems in the context of, for example, an aviation cockpit, where through the windshield visual acuity is critical, it is obvious that the diffractive ghosts and flare should be eliminated or greatly reduced. Also, the construction of the required fast spherical mirrors on the visor is an extremely difficult task. This is particularly so with regard to obtaining repeatability in coating double curvature substrates (visors) and by the optics required to produce the hologram which can require a close to 180 degree cone of illumination.

SUMMARY OF THE INVENTION

The invention is intended to provide a solution and a remedy. It solves the problem of how to provide an ocular protective shield effective in protecting the eyes, with high visual transmission and with minimal flare and ghost imaging. In particular, in accordance with the present invention, it is achieved by using a multiple layer holographic filter in which the angular protection is partitioned and the configuration of the elements introduces a ghost compensating characteristic into the shield. At the same time, this is achieved by a filter design that also has low coloration, high visual transmission of the outside world and simple construction steps and requirements.

BRIEF DESCRIPTION OF THE DRAWINGS

One way of carrying out the invention is described in detail below with reference to drawings which illustrate only two specific embodiments of the invention and in which.

DETAILED DESCRIPTION

Figure 1:
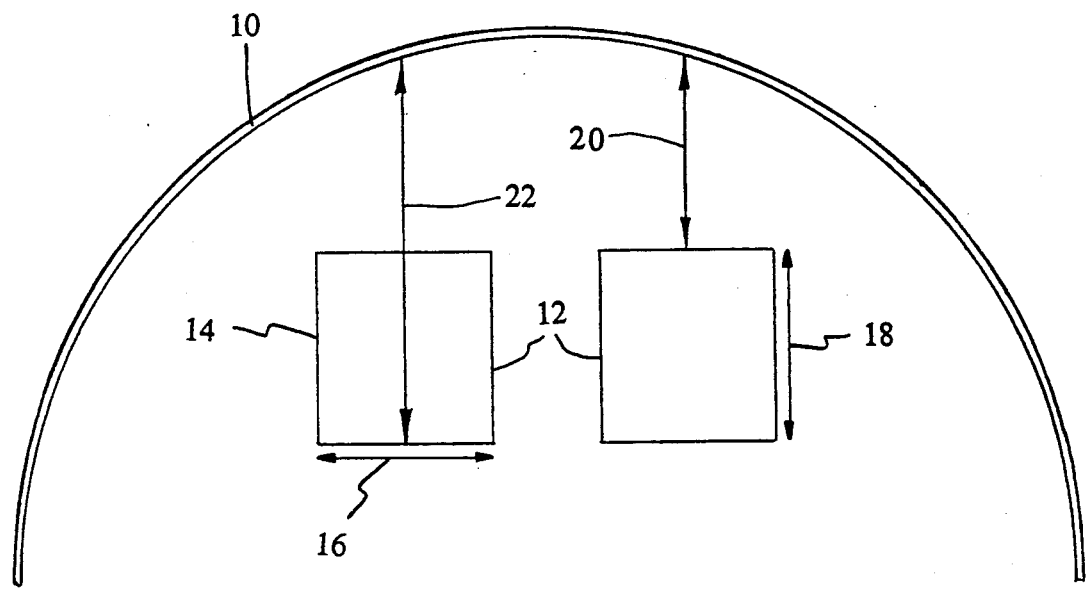
FIG. 1 is a conceptual diagram illustrating safety zones behind a visor.

When the eye position with respect to the filter cannot be kept constant, or the eye/filter configuration must be standard for different size heads, the development of an optimal design becomes critical. The object is to provide with a minimum number of holograms, a filter which provides large angular coverage and allows for eye movement, a large pupil and variation in head dimension, including interpupillary distances (typically 60 mm) and eye relief, as well as average physiological movements.

In addition, to be effective, a holographic filter must not only protect the eye against laser radiation but must also be compatible with the requirements posed by preserving visual transmission in the visible spectrum so that views of the outside world are not impaired and, in the specific case of protecting the eyes of a pilot in an aircraft, the scotopic transmission for effective night vision or under other low level illumination situations, needs to be as high as possible. The filter must also allow for the unrestricted viewing of panels and displays in the cockpit.

In the particular case of a military pilot using a visor with a holographic filter deposited on it, the eye/filter geometry together with considerations regarding anatomic head variations will define a universal safety zone for total eye protection for most all individuals. In particular, an average sized eye is assumed to have a radius, extending from its center of rotation, to the plane of the pupil of 11 mm and a radius from the center of rotation to the anterior surface of the lens of 14 mm for the purpose of calculating an acceptable protected volume.

Likewise, the rotation of the eye is assumed to be ±35 degrees from the axis defined by the center of rotation of the eye and the center of the pupil when the eye is oriented along a line of sight extending parallel to the ground and perpendicular to the line extending between the centers of rotation of the two eyes. For purposes of discussion, this line is sometimes referred to as the visual axis or forward looking eye. This limited range of movement about the visual axis is based upon studies which suggest that objects requiring larger angles of fixation from the visual axis, in order to be viewed, will only be seen after the head starts to move and before the angle of fixation exceeds 35 degrees. For purposes of protective volume definition, the maximum pupil opening is taken as 8 mm in diameter. To accommodate interpupillary distance variations, the maximum interpupillary distance is taken as 64 mm.

Eye relief is defined as the distance between the visor and the eye and is a function of the type of helmet, visor, the position of a visor on the helmet, the fit of the helmet to the pilot's head and the size of the head. Interpupillary distance variations are assumed to be on the order of 9 mm and pupil translation for ±35 degrees eye movement is equal to 20 mm of translation. Adding these figures together yields a safety zone of 37 mm.

For purposes of design, long eye relief distances are not a significance because the angles of incidence with respect to the normal of the visor will always be smaller than for short eye relief distances. The shortest eye relief distance is assumed to be 40 mm. The largest eye relief distance is taken as 80 mm. The above parameters together define a pair of safety zone volumes behind a visor 10, namely, a right eye safety zone 12 and a left eye safety zone 14 of position. The safety zone and each of the safety zones has a width 16 with a magnitude of 37 mm and a depth 18, having a length of 40 mm corresponding to the difference between a short eye relief distance 20 of 40 mm and a long eye relief distance 22 of 80 mm, as illustrated in FIG. 1.

Figure 2:
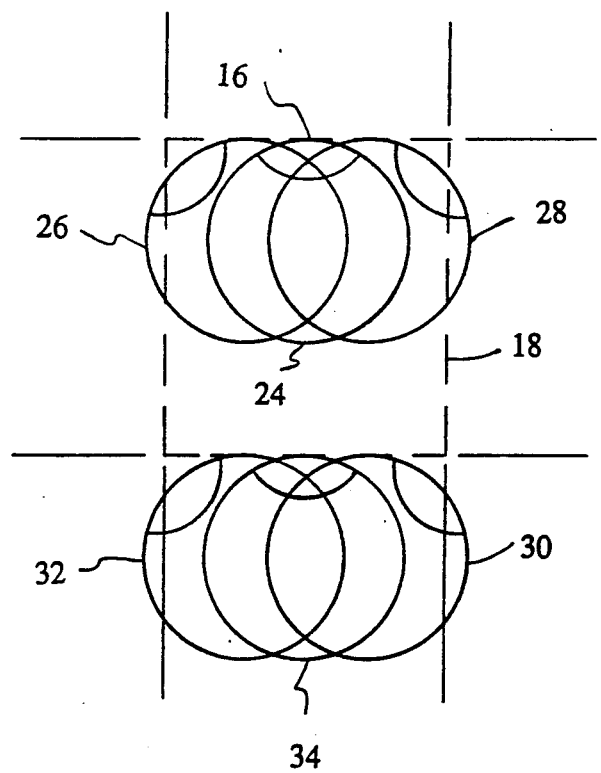
FIG. 2 is a diagram illustrating the definitions of the various parameters forming a safety zone for an eye.

Referring to FIG. 2, the physiological conditions reflected by the definition of the safety zones is illustrated by the various positions of different pilot's eyes behind the visor 10. In particular, centrally positioned short eye relief will result in the position illustrated by eye 24. Interpupillary variations and angular displacement from the visual axis, will cause the eye to move from the positions illustrated at the extremes by eyes 26 and 28.

Similarly, in the case of relatively large eye relief, a centrally positioned eye would take the position illustrated by eye 28 with extremes of angular deviation from the visual axis and displacement from average positions of interpupillary distance yielding the positions illustrated by eyes 30 and 32 in FIG. 2.

As can be inferred from the above discussion, the object of the invention is to provide a highly reflective filter which will reflect primarily the unwanted laser hazard. Generally, the wider the notch, the greater the range of angles over which reflection will occur and, the greater the coloration of the outside world. Obviously, a successful design involves a balancing of these two factors. The shift in wavelength as a function of angle of incidence for a reflective notch may be calculated using the relationship.

$$(n\lambda_i/\lambda_o)^2 = n^2 - \sin^2 i$$

where $\lambda_o$ is the response of the filter at normal incidence to the planes of diffraction, $\lambda_i$ is the response at an angle i and n is the average index of refraction of the hologram. It is noted that the shift in the wavelength becomes proportionately greater for similar changes in angles of incidence at large angles of incidence with respect to the normal.

Figure 3:
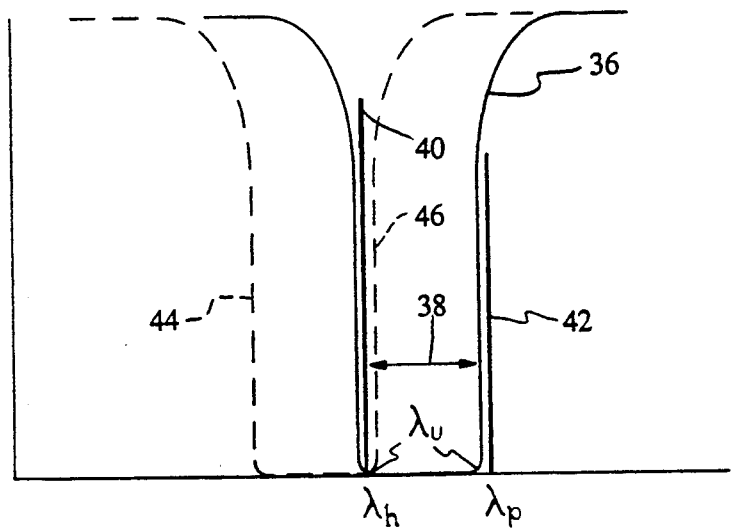
FIG. 3 illustrates the shift of the notch and considerations involved in assuring transmittance of instrumentation signals while protecting against laser hazards in accordance with Bragg's Law.

Insofar as holographic notch wavelengths always shift from longer to shorter wavelengths, if one is designing around a system in which, for example, cockpit instrumentation is provided by a particular phosphor at a particular wavelength, for example, $\lambda_p$ in FIG. 3, the notch 36 in the case of normal incidence would be placed with its upper wavelength limit $\lambda_u$ lower in wavelength than $\lambda_p$. Likewise, the notch would have to have a width 38 wide enough to include the wavelength $\lambda_h$ of a laser radiation hazard 40. Under these circumstances, for normal incidence, a laser radiation hazard would be reflected because it is inside notch 36, but light 42 emanating from the phosphor of aircraft instrumentation would be outside of notch 36 and would be passed substantially without attenuation.

In order for the system to work, for extreme angles of radiation, a displaced notch and a reject range 42 would have to have an upper limit edge 46 at a wavelength $\lambda_U$ which is longer in a wavelength than $\lambda_h$, as illustrated in FIG. 3. In FIG. 3, the displaced reject range 44 is indicated in terms of transmissivity as is the notch 36 shown in solid lines for normal incidence. Laser hazard 40 and phosphor light output 42 is illustrated in terms of wavelength placement and narrowness.

In the case of a possible laser threat at 550 nm, and a phosphor spike at 560 nm, an 8 nanometer notch bandwidth is practical but the above imposed limitations on shift suggest that a maximum angular deviation on the order of about 15 degrees to the planes of diffraction is the maximum range of angles at which the eye may be protected. Thus, a single layer will not provide the safety zones required in view of the considerations discussed above in the simplest cases for visor protection.

Accordingly, the use of holographic geometry in accordance with the invention provide the desired degree of protection. In holographic systems, the optical figure and the configuration of the planes of diffraction are established by the hologram's construction parameters. These parameters are in turn a function of the placement of the point sources or the shape of the wavefronts in the photographic recording of the hologram. Thus, the optical figure will define the direction in which the light will be diffracted and will define the angles between the normals of the optical figure and the direction of light incidence. If the normals to the optical figure, which are identical to the normals to the planes of diffraction, are considered, then the directions of diffraction and reflection will coincide to a first approximation.

The spectral response of a hologram depends primarily on the spacing of the planes of diffraction. This spacing is a function of the construction parameters and may be determined by Bragg's Law:

$$2nd \sin \theta = \lambda$$

where n is the index of refraction in the medium, d is the spacing recorded in the hologram, $\lambda = \lambda_\theta$ is the laser wavelength used in recording the hologram and $\theta$ is the Bragg angle or half the interbeam of the angle of the interfering wavefront. After recording, spacing is fixed and there is a strict relationship between $\theta$ and the wavelength response $\lambda_i$ of the hologram. In the case of reflection holograms, $\theta$ becomes the complement of the angle of incidence in the medium, with respect to the normal to the planes of diffraction.

The spacing of the planes of diffraction can be constructed constant over the entire hologram or constructed having a gradient or continuous variation as discussed above.

Figure 4:
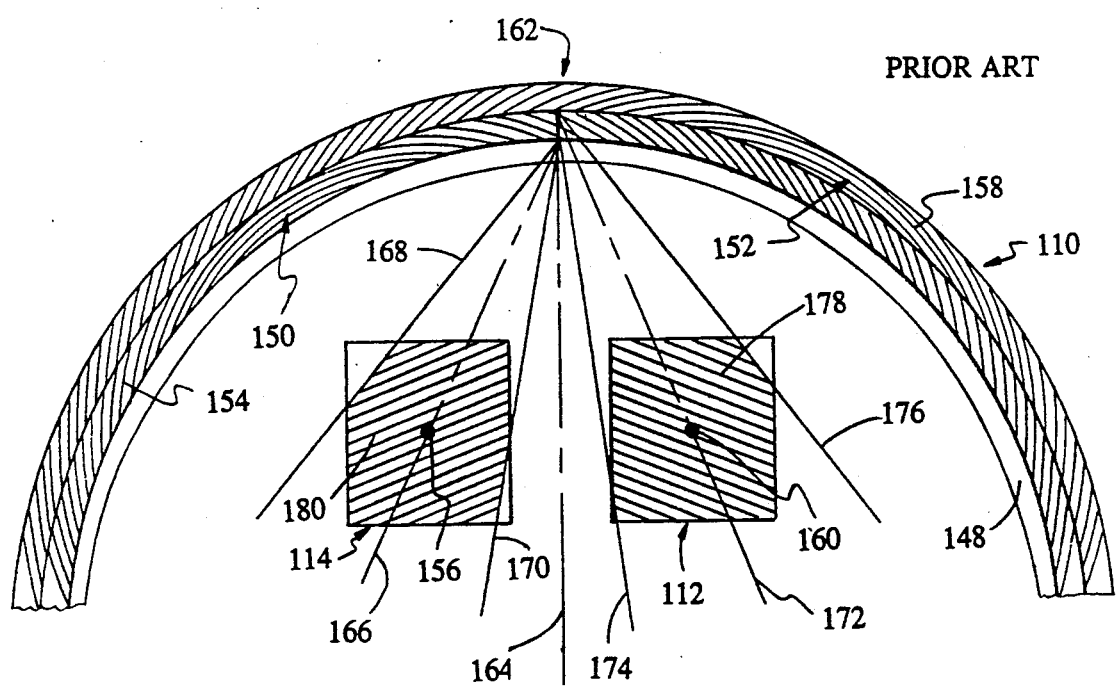
FIG. 4 is a prior state of the art approach incorporating a laser protective two-layer hologram on a visor.

For purposes of understanding the present invention, it is helpful to consider the prior art system illustrated in FIG. 4, where the planes of diffraction are not identical and symmetrically opposite at each point on the visor, thus not providing for ghost compensation. Here, a visor 110 comprising a transparent substrate 148 which includes a left eye protective holographic layer 150 and a right eye protective holographic layer 152 is formed holographically. Generally, left protective layer 150 has been holographically formed to include a spherical optical figure comprising numerous diffractive layers 154 which together define a plurality of spheres centered at point 156. Similarly, a plurality of diffractive layers 158 are disposed in layer 152 and generally defined spheres centered on point 160.

Using the above analysis, we can define a right eye safety zone 112 and a left eye safety zone 114 which the present invention is aimed at achieving. If we consider a point 162 on the visor, which is defined by the intersection of visor 110 with a line 164 parallel to the visual axes of the viewer's eyes and centered therebetween, we note that at that point a first normal 166 is defined perpendicular to the plane in refractive layers 154 with limits of protection defined between limit boundaries 168 and 170. Likewise, a normal 172 to the refractive layers 158 in protective layer 152 defines a range of protection between limit boundaries 174 and 176.

As can be seen from FIG. 4, nearly acceptable volumes of eye protection are provided as are indicated by the slanted lines 178 and 180 in right eye safety zone 112 and left eye safety zone 114. This is for a notch width of both holograms of about 8 nm corresponding to an angular coverage of ±15° away from the normal. This description and coverage applies only to light entering point 162 of the visor. Similar arguments can be made for any other points on the visor, but the volume of protection will be different and greatly reduced at some points and/or angles of incidence.

As was discussed above, the above solution, while it does not provide the protective volume needed in a helmet visor, additionally suffers from the inadequacies of substantial flare and diffractive ghosts, produced by a surface grating caused by the intersection of the planes of diffraction with the surface of the holographic optical element. Also required are expensive tooling (to avoid multiple recordings during construction of the hologram) and very fast optics to produce these holograms on the visor substrate or visor shape (without transfer).

Figure 5:
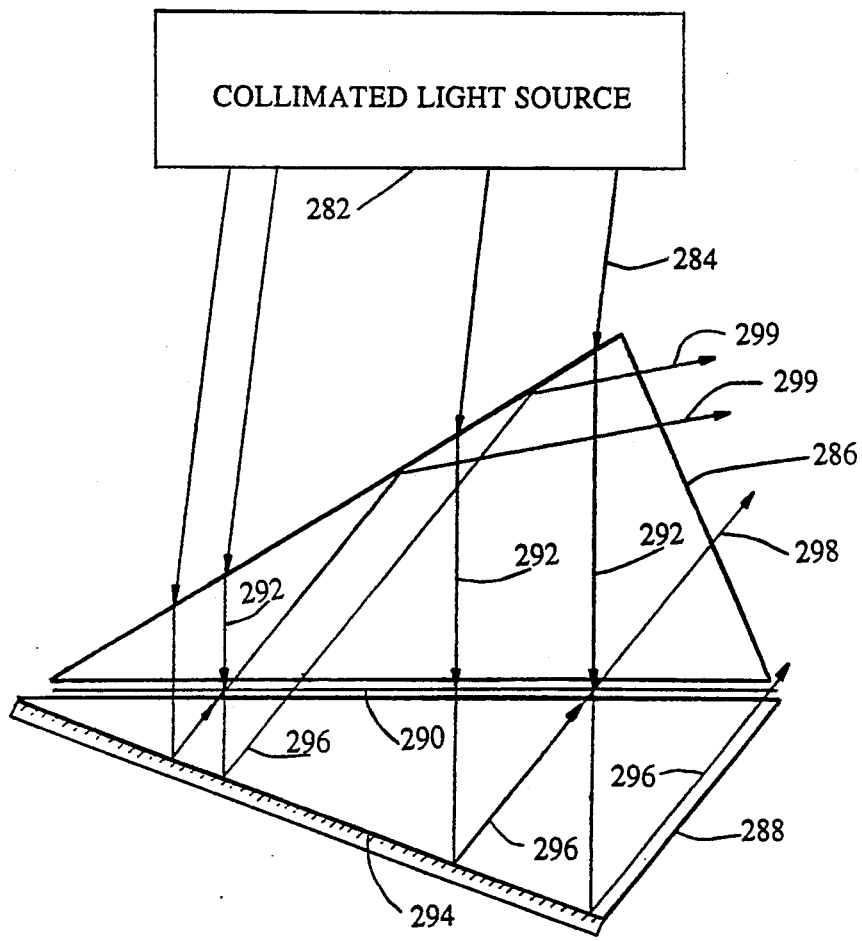
FIG. 5 illustrates the tool for construction of a slanted holographic mirror for use in the present invention.

In accordance with the present invention, the recording of the holographic notch filter is achieved without multiple internal reflections and resultant multiple recordings using the construction geometry illustrated in FIG. 5. The advantage of this system is that the absence of multiple recordings greatly reduces undesired images (ghosts) in the system. Generally, the system includes a source of collimated or parallel light rays 282 outputting a parallel light wave bundle 284 which impinges on a prism 286. Prism 286 faces a prism 288 onto which a sensitive holographic emulsion has been coated. The holographic optical element constructed with this geometry is known as a slanted holographic plane mirror.

During a recording of the hologram, light source 282 is activated causing rays in bundle 284 to fall upon prism 286 pass through prism 286 as refracted light rays 292 which, in turn, are reflected by the reflective coating 294 on prism 288. They then are reflected refracted light rays 296 which interfere with refracted light rays 292 to form diffractive planes in holographic emulsion layer 290. These planes have an orientation perpendicular to the bisector between reflected refracted light rays 296 and refracted rays 292. The reflected refracted light rays then pass out from prism 286 either directly as in the case of light rays 298 or after reflection as in the case of light rays 299. The angle between the surface of the hologram and the planes of diffraction is the slant angle and is related to the angle of the prism face which is mirror coated. The slant angle used in this invention is about 20° inside the hologram.

The hologram thus produced is then developed in conventional form. While it is possible to use a dichromated gelatin emulsion to form the sensitive holographic emulsion layer 290, newly developed photopolymers (such as the ones produced by Dupont Co. or Polaroid Co.) may also be used.

After construction of the hologram and development in accordance with the technique required for the particular recording material used, the hologram may be transferred in accordance with the techniques described in my earlier U.S. Pat. No. 4,802,719, issued Feb. 7, 1989 and directed to an infra-red laser shield or, in a similar way, using a photopolymer. For example, with the Dupont photopolymer, the hologram is produced on a plane glass substrate or prismatic substrate, developed and removed from the substrate after it has been plastified (to avoid breaking the brittle photopolymer when it is dry) and transferred to the visor substrate, in an unsupported way or by using a flexible or heat formable carrier.

The hologram produced by the construction optics of FIG. 5 is generally a uniformly slanted hologram which has the shape of holographic emulsion layer 290. The dry process photopolymer, such as the one produced by Dupont, is believed to have a more controllable development process and thus gives superior results as compared to dichromated gelatin, which tends to form surface defects which are a primary source of flare. Generally, this flare is believed to be the result of small frequency surface gratings which appear at the surface of developed holographic layers.

Figure 6:
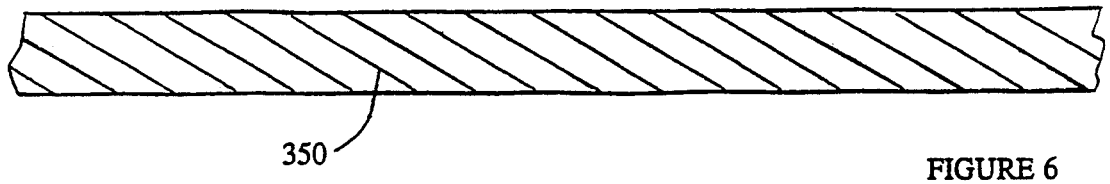
FIG. 6 illustrates a holographic mirror with the slanted planes of diffraction constructed with the apparatus of FIG. 5.
Figure 7:
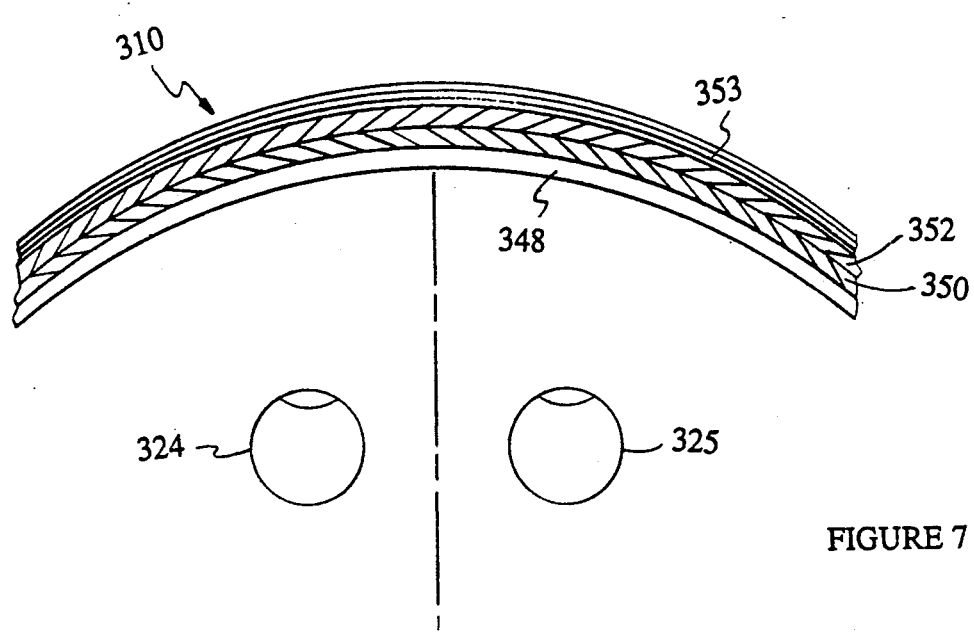
FIG. 7 illustrates a protective visor constructed in accordance with the present invention.
Figure 8:
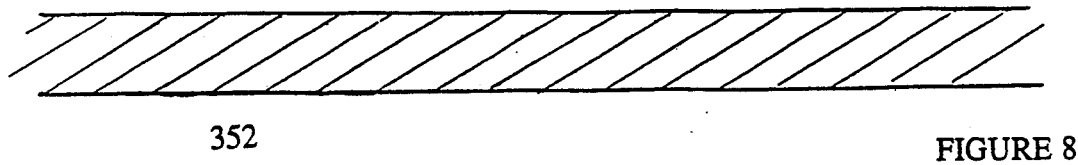
FIG. 8 is a view of another layer to be incorporated into the inventive device.
Figure 10:
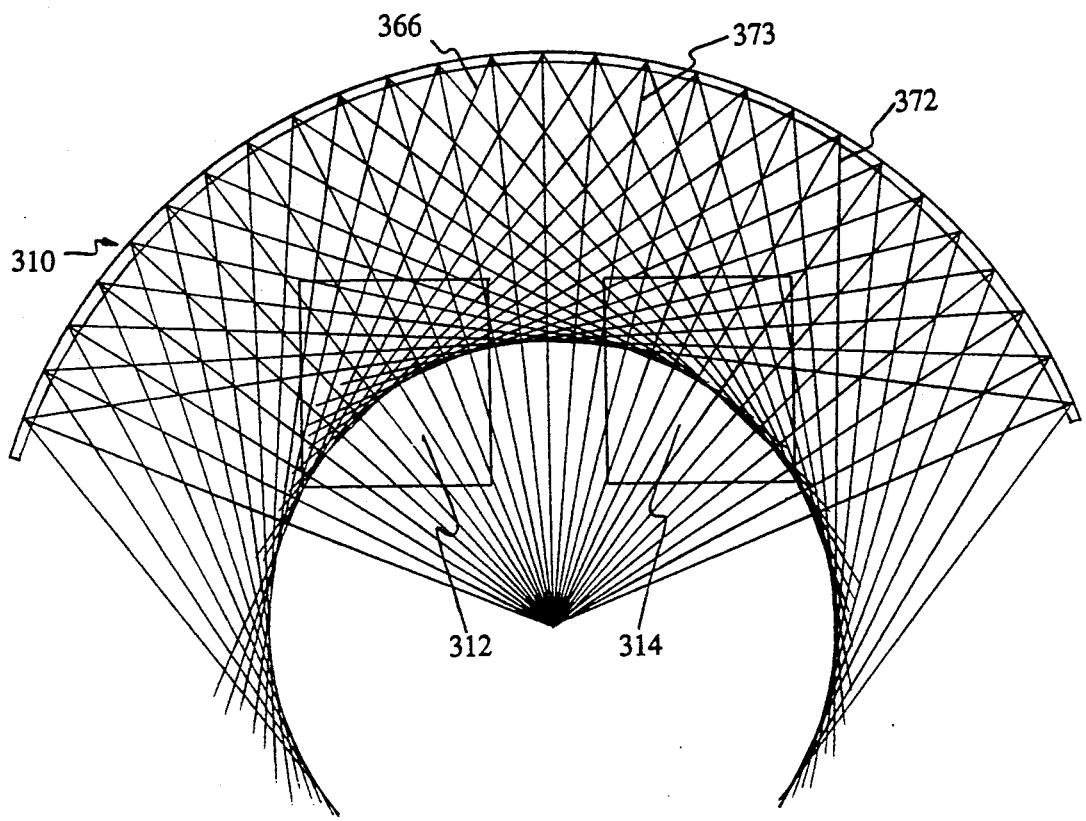
FIG. 10 is a graphic device to calculate the protection given for the filter on the visor of FIG. 7.

A holographic layer formed by the construction optics of FIG. 5 is illustrated in FIG. 6. A transparent substrate 348 receives this layer 350 which functions primarily as a left-eye protective layer, as illustrated in FIG. 7 and FIG. 10. Rotating a layer (such as the one in FIG. 6) 180° horizontally, we obtain the other holographic layer, in FIG. 8. This filter layer 352 serves primarily as a right-eye protective layer and is adhered over layer 350 to provide protection primarily to the right eye of a person using the visor.

Finally, the structure (while useful as a two layer device in some applications) is completed with a plane holographic notch filter which is the analog of an unslanted plane mirror. Such a plane holographic mirror layer 353 is transferred onto visor 348 to achieve a three-layer structure for the protection of the eyes 324 and 325 of a person wearing the shield.

Figure 9:
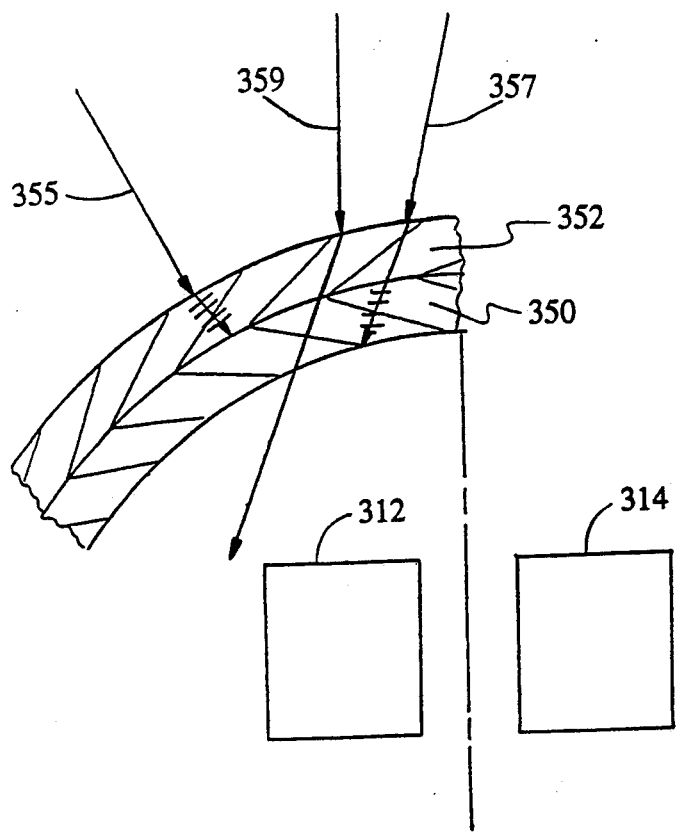
FIG. 9 illustrates the surface diffractive ghosts of two of the layers of the embodiment of FIG. 7.

It is noted that in FIG. 7, as in other figures, the illustrated size of the thickness of the holographic notch filter layers is greatly exaggerated in order to illustrate their principles of operation. Such operation may be most easily understood with reference to FIG. 9, which shows how "diffractive ghosts", even when not totally compensated, cannot damage the eye. Generally, light impinging upon the holographic layers will either take the form of light rays 355 which are reflected by layer 352 or light rays 357 which are reflected by layer 350. Although some light rays such as light rays 359 will pass through the visor, they will not pass through the safety zones 312 or 314. For simplicity of illustration, only the slanted plane mirrors are illustrated in FIG. 9.

A more complete consideration of the reflective notch system of the present invention is illustrated in FIG. 10. In particular, FIG. 10 illustrates for a visor incorporating multiple protective holographic layers, (including, layers formed on a planar substrate as oppositely slanted right and left mirrors and a planar mirror), the normals to the optical surfaces of the various layers of the visor.

For simplicity of illustration, the visor is shown as a single substantially transparent member without the individual layers being shown. In particular, FIG. 10 illustrates normals 366 perpendicular to the planes of diffraction in left eye protective layer 350 and normals 372 which are perpendicular to the planes of diffraction in right eye protective layer 352. Similarly, it illustrates normals 373 perpendicular to the planes of diffraction of the unslanted mirror 353. Insofar as there is a range of angular coverage (corresponding to the notch width) around all of these normals, with each point defining substantially a protected cone extending about 15 degrees (for an 8 nm notch width) around the normal at that given point, the safety zones 312 and 314 are substantially completely protected.

As can be seen in FIG. 7, in contrast with the prior art system illustrated in FIG. 4, the surface gratings between sensitive layers 350 and 352 ar identical and opposite if we consider any local region. This configuration will produce identical but opposite surface gratings in the slanted elements, creating a compensation of the surface diffracted ghosts.

Even in the event that total compensation is not achieved, ghosts at the laser wavelength cannot be produced or transmitted through the filter towards the eyes. If ghosts are produced by the first or second surface grating of the first hologram, they will be returned in the incident laser direction and in any case will be reflected by the second hologram if the same are aimed toward the eye. See FIG. 9. Ghosts produced at the first surface grating of the second hologram, if heading toward an eye, will also be reflected by the hologram. The last surface grating cannot produce a ghost which heads toward the eye because light cannot reach that grating at the protected angles. In other words, if the zero order is transmitted (in the direction of incidence) it will produce a ghost (first order) but, if directed toward the eye, will be stopped by the second hologram. If the second hologram is oriented to the other eye and cannot stop this ghost, it means that this ghost never could have reached the second hologram because in this direction it would have been blocked by the first hologram.

Generally, the system has this characteristic because the slanted planes are oriented to protect the eyes and the ghosts are diffracted at angles related to the slant. This is the case because the slant produces surface gratings which are oppositely oriented and have the same constant frequency in any local region of the helmet visor.

In connection with the above, it is noted that because the third layer 353 is formed as a planar unslanted mirror and then reformed into a mirror with power when transferred to the substrate, as illustrated in FIG. 7, it provides a part of the solution, principally in the case of the shortest eye relief configurations. The inventive three-layer system, which includes the unslanted, conformal mirror, increases the coverage to a "practical" total coverage for a standardized filter.

Figure 11:
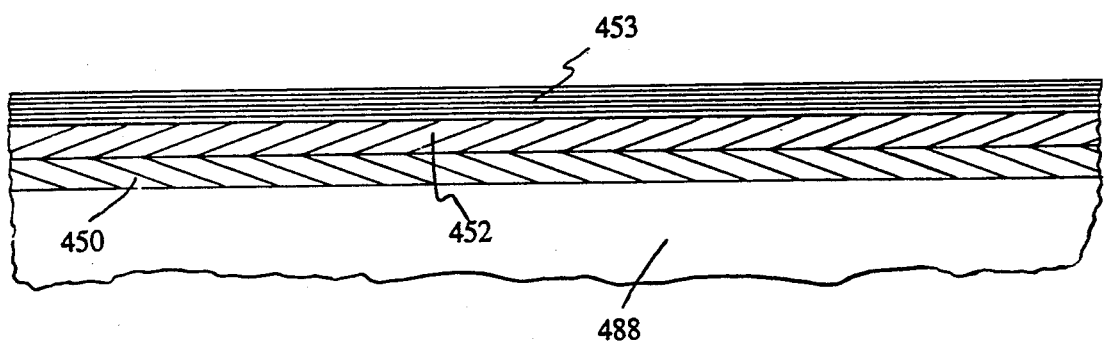
FIG. 11 illustrates the first step in the fabrication of the inventive holographic filter for the visor.

An alternative approach toward forming the visor whose operation is illustrated in FIG. 10, is given in FIG. 11. In particular, in accordance with this approach, layers 450, 452 and 453 are formed one over another on a planar substrate 488, and transferred to a curved visor in a single transfer operation, instead of singly transferring each of the layers separately. The three layers adhered to the substrate may even be bent with the substrate to conform to a helmet visor and laminated to the visor using heat, glue or any other lamination technique.

While an illustrative embodiment of the invention has been described above, it is, of course, understood that various modifications will be apparent to those of ordinary skill in the art. Such modifications are within the spirit and scope of the invention, which is limited and defined only by the appended claims.

We claim:

1. A holographic optical element comprising a first holographic layer having planes of diffraction oriented in a first direction in a given local area and a second holographic layer disposed over said first holographic layer and having planes of diffraction oriented in said local area in the opposite direction, said first holographic layer comprising the holographic analog of a slanted mirror and said second holographic layer comprising the holographic analog of an oppositely slanted mirror, said slant and said opposite slant having substantially the same magnitude of slant but opposite orientation, said first and second holographic layers conforming to and adhered to the visor of a helmet and said slant and said opposite slant being substantially constant with respect to a tangent to the surface of said visor, said visor being disposed about a pair of eyes of a person wearing said visor, said slanted mirrors being constructed as planar mirrors, and then bent to conform to a curve disposed about said pair of eyes to act as nonplanar slanted mirrors.

2. A holographic optical element comprising a first holographic layer having planes of diffraction oriented in a first direction in a given local area and a second holographic layer disposed over said first holographic layer and having planes of diffraction oriented in said local area in the opposite direction, said first holographic layer comprising the holographic analog of a slanted mirror and said second holographic layer comprising the holographic analog of an oppositely slanted mirror, said slant and said opposite slant having substantially the same magnitude of slant but opposite orientation, said holographic analogs of slanted mirrors being locally planar.

3. A holographic optical element, as in claim 2, wherein the magnitude of the slant is about 20 degrees inside each layer.

4. A holographic optical element comprising a first holographic layer having planes of diffraction oriented in a first direction in a given local area and a second holographic layer disposed over said first holographic layer and having planes of diffraction oriented in said local area in the opposite direction, said planes of diffraction in said first and second holographic layers being of substantially equal magnitude but opposite orientation in substantially all areas where said first holographic layer overlies said second holographic layer.

5. A holographic optical element comprising a first holographic layer having planes of diffraction oriented in a first direction in a given local area and a second holographic layer disposed over said first holographic layer and having planes of diffraction oriented in said local area in the opposite direction, said first holographic layer comprising the holographic analog of a slanted mirror and said second holographic layer comprising the holographic analog of an oppositely slanted mirror, said slant and said opposite slant having substantially the same magnitude of slant but opposite orientation, and a third holographic layer secured to said first and second holographic layers and defining planes of diffraction substantially parallel to the surface of said third holographic optical layer.

* * * * *